United States Patent
Padgett et al.

(10) Patent No.: US 6,766,259 B2
(45) Date of Patent: Jul. 20, 2004

(54) SYSTEM AND A METHOD FOR DETECTING FIBER DAMAGE IN A DIALYZER

(75) Inventors: William Brandon Padgett, Mountain Home, AR (US); Ralph Steven Kesler, Mountain Home, AR (US); Michael E. Cameron, Mountain Home, AR (US); Roger D. Horton, Mountain Home, AR (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/208,061

(22) Filed: Jul. 29, 2002

(65) Prior Publication Data

US 2004/0019438 A1 Jan. 29, 2004

(51) Int. Cl.[7] .............................................. G06F 19/00
(52) U.S. Cl. .................... 702/35; 210/143; 210/321.72; 210/321.79; 374/5
(58) Field of Search .............................. 702/33–36, 39, 702/42, 43, 56, 51, 75–77, 103, 109, 110–116, 170, 171, 179, 180; 73/38, 40, 48.5 A, 49.2, 865.9; 250/338.5; 356/51; 374/5, 131; 134/18; 137/340; 210/85, 143, 86, 87, 646, 739, 741; 604/4.01, 99.01, 6.05

(56) References Cited

U.S. PATENT DOCUMENTS

| | | |
|---|---|---|
| 3,172,285 A | 3/1965 | Dietert et al. ................... 73/38 |
| 3,234,045 A | 2/1966 | Larsen ........................ 427/105 |
| 3,350,920 A | 11/1967 | Brauer ........................ 73/49.1 |
| 3,392,573 A | 7/1968 | Benson et al. ................. 73/38 |
| 3,483,735 A | 12/1969 | Packo ......................... 73/40.7 |
| 3,505,876 A | 4/1970 | Niebergall .................. 73/865.9 |
| 3,847,013 A | 11/1974 | Luy ............................ 73/40.7 |
| 3,960,001 A | 6/1976 | Hayes ........................ 73/40.7 |

(List continued on next page.)

FOREIGN PATENT DOCUMENTS

| | | |
|---|---|---|
| EP | 623357 A1 | 11/1994 |
| EP | 750938 | 1/1997 |
| FR | 2671184 A1 | 12/1990 |
| JP | 53134776 | 11/1978 |
| JP | 54138874 | 10/1979 |
| JP | 6117957 | 4/1994 |
| JP | 10244000 | 9/1998 |
| JP | 10258120 | 9/1998 |
| JP | 2001145281 | 5/2001 |
| WO | WO9015631 A1 | 12/1990 |
| WO | WO9528184 A1 | 10/1995 |
| WO | WO9624214 | 8/1996 |
| WO | WO971171 | 4/1997 |

*Primary Examiner*—John Barlow
*Assistant Examiner*—John Le
(74) *Attorney, Agent, or Firm*—Paula J. F. Kelly; Joseph P. Reagen; Bell, Boyd & Lloyd LLC

(57) ABSTRACT

A system and a method are provided for detecting fiber damage in a dialyzer. The system may have a device which may transmit a gas into an interior of a fiber within a dialyzer. The temperature of the gas may be different than a temperature of the dialyzer. A thermal imaging camera may detect a temperature difference at a surface of the fiber where the gas may be escaping. The thermal imaging camera may be connected to a monitor which enables a user to view a location of the difference in temperature. As a result, the user may locate the damaged area of the fiber. The user may then repair the damaged area.

20 Claims, 5 Drawing Sheets

U.S. PATENT DOCUMENTS

| | | | |
|---|---|---|---|
| 4,134,290 A | 1/1979 | Bauerle | 73/40.5 R |
| 4,188,117 A | 2/1980 | Yamauchi et al. | 356/237.1 |
| 4,188,817 A | 2/1980 | Steigelmann | 73/40.7 |
| 4,213,768 A | 7/1980 | Bauman et al. | 95/273 |
| 4,324,568 A | 4/1982 | Wilcox et al. | 95/286 |
| 4,332,264 A | 6/1982 | Gortz et al. | 134/57 R |
| 4,382,378 A | 5/1983 | Wadsworth et al. | 73/38 |
| 4,402,214 A | 9/1983 | Morgan et al. | 73/40.7 |
| 4,429,566 A | 2/1984 | Armell et al. | 73/40.7 |
| 4,444,596 A | 4/1984 | Gortz et al. | 134/18 |
| 4,444,597 A | 4/1984 | Gortz et al. | 134/18 |
| 4,445,364 A | 5/1984 | Stieff et al. | 73/40.7 |
| 4,449,392 A | 5/1984 | Huschke | 73/40 |
| 4,490,053 A * | 12/1984 | Coston et al. | 374/5 |
| 4,493,207 A | 1/1985 | Dempsey | 73/40.7 |
| 4,494,403 A | 1/1985 | Bowers et al. | 73/40.7 |
| 4,515,007 A | 5/1985 | Herman | 73/38 |
| 4,524,607 A | 6/1985 | Pelletier et al. | 73/40.5 R |
| RE31,952 E | 7/1985 | Wilcox et al. | 73/40.7 |
| 4,586,376 A | 5/1986 | Outmans | 73/865.8 |
| 4,604,208 A | 8/1986 | Chu et al. | 210/636 |
| 4,612,798 A | 9/1986 | Roberts | 73/40.7 |
| 4,619,136 A | 10/1986 | Ortiz | 73/38 |
| 4,676,092 A | 6/1987 | Tuttle | 73/38 |
| 4,686,848 A | 8/1987 | Casselberry et al. | 73/38 |
| 4,745,797 A | 5/1988 | Wegrzyn | 73/40.7 |
| 4,754,638 A | 7/1988 | Brayman et al. | 73/40.7 |
| 4,875,360 A | 10/1989 | Ziemer | 73/40.7 |
| 4,884,438 A | 12/1989 | Jones et al. | 73/152.11 |
| 4,888,115 A | 12/1989 | Marinaccio et al. | 210/636 |
| 4,918,975 A | 4/1990 | Voss | 73/40.7 |
| 4,944,180 A | 7/1990 | Tou et al. | 73/38 |
| 4,969,350 A | 11/1990 | Fogal, Sr. | 73/40.7 |
| 5,073,482 A | 12/1991 | Goldstein | 435/5 |
| 5,102,434 A | 4/1992 | Hijikata et al. | 95/273 |
| 5,114,580 A | 5/1992 | Ahmad et al. | 210/646 |
| 5,138,871 A | 8/1992 | Retta et al. | 73/38 |
| 5,205,156 A | 4/1993 | Asano et al. | 73/38 |
| 5,247,434 A | 9/1993 | Peterson et al. | 700/83 |
| 5,252,213 A | 10/1993 | Ahmad et al. | 210/542 |
| 5,282,380 A | 2/1994 | DiLeo et al. | 73/38 |
| 5,306,913 A * | 4/1994 | Noach et al. | 250/338.5 |
| 5,326,476 A | 7/1994 | Grogan et al. | 210/646 |
| 5,398,541 A | 3/1995 | Hijikata et al. | 73/38 |
| 5,411,682 A | 5/1995 | Nagashima | 264/36.15 |
| 5,487,827 A | 1/1996 | Peterson et al. | 210/87 |
| 5,522,930 A | 6/1996 | Modera et al. | 118/317 |
| 5,580,460 A | 12/1996 | Polaschegg | 210/646 |
| 5,581,017 A | 12/1996 | Bejtlich, III | 73/38 |
| 5,587,521 A | 12/1996 | Lanasa | 73/49.1 |
| 5,618,991 A | 4/1997 | Levinrad | 73/40.7 |
| 5,621,524 A | 4/1997 | Mitani | 356/338 |
| 5,640,236 A | 6/1997 | Nagashima | 356/237.1 |
| 5,670,050 A * | 9/1997 | Brose et al. | 210/646 |
| 5,674,404 A | 10/1997 | Kenley et al. | 210/741 |
| 5,681,984 A | 10/1997 | Cavestri | 73/40.7 |
| 5,711,883 A | 1/1998 | Folden et al. | 210/646 |
| 5,739,420 A | 4/1998 | Peterson | 73/40.512 |
| 5,763,765 A | 6/1998 | Lamont et al. | 73/40.7 |
| 5,808,181 A | 9/1998 | Wamsiedler et al. | 73/38 |
| 5,821,404 A | 10/1998 | Bohm et al. | 73/40.7 |
| 5,835,976 A | 11/1998 | Kent et al. | 73/40.7 |
| 5,847,821 A | 12/1998 | Tracy et al. | 356/237.1 |
| 5,850,037 A | 12/1998 | Mullins | 73/40.5 R |
| 5,861,547 A | 1/1999 | Kawai et al. | 73/49.2 |
| 5,892,142 A | 4/1999 | Ghorashi et al. | 73/38 |
| 5,908,993 A | 6/1999 | Takeshima et al. | 73/865.5 |
| 5,938,929 A | 8/1999 | Shimagaki et al. | 210/645 |
| 5,974,860 A | 11/1999 | Kuroda et al. | 73/40 |
| 6,036,668 A | 3/2000 | Mathis | 604/29 |
| 6,050,133 A | 4/2000 | Achter et al. | 73/40.7 |
| 6,066,261 A | 5/2000 | Spickerman | 210/739 |
| 6,103,117 A | 8/2000 | Shimagaki et al. | 210/321.71 |
| RE36,914 E | 10/2000 | Carlsen et al. | 210/321.79 |
| 6,187,207 B1 | 2/2001 | Brauer | 210/739 |
| 6,223,130 B1 | 4/2001 | Gray et al. | 702/51 |
| 6,236,747 B1 | 5/2001 | King et al. | 382/149 |
| 6,254,787 B1 | 7/2001 | Kimura et al. | 210/748 |
| 6,257,048 B1 | 7/2001 | Hietala et al. | 73/24.01 |
| 6,269,681 B1 | 8/2001 | Hara et al. | 73/38 |
| 6,280,632 B1 | 8/2001 | Polaschegg | 210/739 |
| 6,284,131 B1 * | 9/2001 | Hogard et al. | 210/143 |
| 6,327,895 B1 | 12/2001 | Jeppsson et al. | 73/40 |

\* cited by examiner

US 6,766,259 B2

SYSTEM AND A METHOD FOR DETECTING FIBER DAMAGE IN A DIALYZER

BACKGROUND OF THE INVENTION

The present invention relates to a system and a method for detecting fiber damage in a dialyzer. More specifically, the system has a device which may inject a gas into a dialyzer having a fiber within the dialyzer. The gas may escape through a damaged area of the fiber. A device, such as a thermal imaging camera, may detect a temperature variation at an exterior of the fiber at which point the gas is escaping. A variation in temperature may signify that the fiber is damaged. The damaged area may then be located and repaired.

It is generally known to introduce fluids into the body, including medicaments and supplements, as well as bodily fluids, such as blood, plasma or the like. Often, a fluid delivery system is used to introduce these materials. An example of a fluid delivery system may be a dialysis system. A dialyzer may be implemented within the dialysis system to purify blood or other fluids.

A known dialyzer may have a tube having an inlet dialysate port at one side of the dialyzer and an outlet dialysate port at an opposite side. The inlet dialysate port may allow the entry of dialysate, i.e., a fluid for purifying blood into the dialyzer. The outlet dialysate port may allow the dialysate to leave the dialyzer. The dialyzer may also contain fibers which may have a tube-like shape. The fibers may house fluids such as blood, plasma or the like. Fluids within the fibers may travel in a first direction while dialysate within the dialyzer may travel in an opposite direction exterior to the fibers. The dialysate may contain elements which may potentially contaminate blood. Therefore, contact between the dialysate and the blood within the fibers should be avoided. Thus, for efficient dialysis to occur, the fibers of the dialyzer must be devoid of leaks and/or damage.

A known method for detecting leaks in a dialyzer involves placing the dialyzer in a fluid bath. The dialyzer is subsequently examined for bubbles which may form at a surface of a damaged area when air escapes from the damaged area. However, the fluid bath may contain contaminants. As a result, contacting the dialyzer with the fluid bath may introduce the contaminants into the dialyzer. In addition, determining an exact location of the damaged area of a dialyzer based on the location of bubbles at the surface of the fiber may be difficult and/or time-consuming.

A need, therefore, exists for a system and a method for detecting fiber damage in a dialyzer which enables a user to detect fiber damage in a dialyzer without exposing the dialyzer to contaminants. A further need exists for a system and a method for detecting fiber damage in a dialyzer which enables the user to determine the specific location of a damaged area of the dialyzer. A need also exists for a system and a method for detecting fiber damage in a dialyzer which enables detection of the damaged area in an efficient manner.

SUMMARY OF THE INVENTION

The present invention relates to a system and a method for detecting fiber damage in a dialyzer. The system has a device which may transmit a gas into the interior of a dialyzer. The temperature of the gas is different than that at an exterior of the fiber prior to injection of the gas. A device, such as, for example, a thermal imaging camera, may detect a temperature variation at the exterior of the fiber where the gas may be escaping. The thermal imaging camera may be connected to a monitor on which a user may view the variations in temperature. The variations may be represented by, for example, distinct areas on a screen of the monitor and may signify a damaged area of the fiber. The user may then locate the damaged area and may repair the same.

To this end, in an embodiment of the present invention, a method is provided for detecting fiber damage in a dialyzer having a body defining an interior and further having a fiber having an interior wherein the fiber is within the interior of the dialyzer and wherein the fiber has a damaged area. The method comprises the steps of: transmitting a gas into the interior of the fiber wherein the gas is at a temperature different from a temperature of the dialyzer and wherein the gas exits the fiber through the damaged area; and detecting a difference in temperature between a temperature at a surface of the fiber where the gas is exiting the damaged area and a temperature of the dialyzer.

In an embodiment, the method comprises an additional step of displaying the difference in temperature on a monitor.

In an embodiment, the method comprises an additional step of heating the dialyzer prior to transmitting the gas into the interior of the dialyzer.

In an embodiment, the method comprises an additional step of cooling the dialyzer prior to transmitting the gas into the interior of the dialyzer.

In an embodiment, the method comprises an additional step of directing a laser toward the location of the damaged area.

In an embodiment, the method comprises an additional step of recording the location of the damaged area of the dialyzer.

In an embodiment, the method comprises an additional step of controlling the gas transmitted into the interior of the fiber.

In an embodiment, the method comprises an additional step of moving the dialyzer to locate the difference in temperature.

In an embodiment, the method comprises an additional step of indexing the location of the damaged area.

In an embodiment, the method comprises an additional step of repairing the damaged area.

In an embodiment, the method comprises an additional step of sealing the fiber.

In an embodiment, the method comprises an additional step of contacting the damaged area with a heated tip.

In an embodiment, the method comprises an additional step of varying the temperature of the gas.

In another embodiment of the present invention, a system is provided for detecting a damaged area. The system has a dialyzer having an interior and further having a fiber within the interior wherein the fiber is defined by an interior and wherein the fiber has a damaged area through which a gas may escape. The system also has a heater which transmits the gas into the interior of the fiber. In addition, the system has a thermal imaging camera which detects a difference in temperature between a temperature of the gas at a location of the damaged area and a temperature of a surface of the dialyzer.

In an embodiment, the system has a monitor connected to the thermal imaging camera.

In an embodiment, the system has a heat sink adjacent to the dialyzer.

In an embodiment, the system has a positioning apparatus for moving the dialyzer adjacent to the thermal imaging camera.

In an embodiment, the system has a laser adjacent to the thermal imaging camera wherein the laser indicates the location of the damaged area.

In another embodiment of the present invention, a method is provided for determining a location of a damaged area of a dialyzer. The method comprises the steps of: creating a temperature change in an interior of the dialyzer; viewing a location of the temperature change; and assigning a coordinate to the location of the change in temperature.

In an embodiment, the method comprises an additional step of indexing the coordinate.

It is, therefore, an advantage of the present invention to provide a system and a method for detecting fiber damage in a dialyzer which enables a user to detect damage in a fiber of a dialyzer without contaminating the dialyzer.

Another advantage of the present invention is to provide a system and a method for detecting fiber damage in a dialyzer which enables a user to locate where a fiber is damaged.

Yet another advantage of the present invention is to provide a system and a method for detecting fiber damage in a dialyzer which decreases the amount of time required to detect a damaged area of a fiber.

A still further advantage of the present invention is to provide a system and a method for detecting fiber damage in a dialyzer which enables a user to repair a damaged area of a dialyzer.

Moreover, an advantage of the present invention is to provide a system and a method for detecting fiber damage in a dialyzer which enables a user to locate where a fiber may be repaired.

And, another advantage of the present invention is to provide a system and a method for detecting fiber damage in a dialyzer which enables a user to repair a damaged area of a dialyzer manually or automatically.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to a system and a method for detecting fiber damage in a dialyzer. A gas may be injected into an interior of the dialyzer. Temperature of the gas may be different than a temperature of the dialyzer. A thermal imaging camera may be positioned adjacent to the dialyzer. The thermal imaging camera may detect temperature variations at an exterior, or surface, of the fiber where the gas may be escaping from the fiber. The variations in temperature may be displayed on a monitor connected to the thermal imaging camera in the form of, for example, distinctly colored areas. The areas may represent a damaged area of the fiber where injected gas may be escaping. A user may then record a location of the damaged area and/or may repair the same by, for example, sealing the damaged area.

Figure 1:
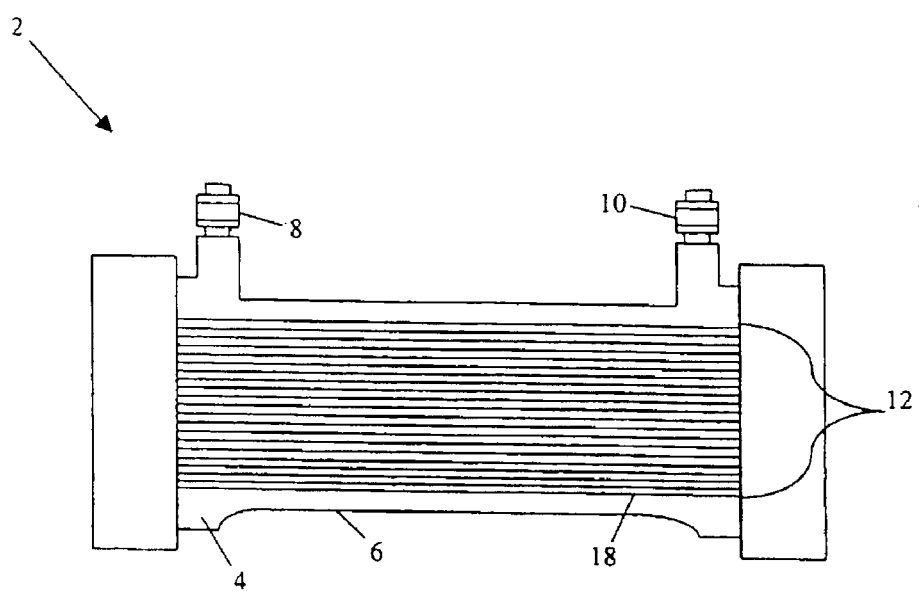
FIG. 1 illustrates a cross-sectional view of a dialyzer in an embodiment of the present invention.

Referring now to the drawings, wherein like numerals refer to like parts, FIG. 1 illustrates a dialyzer 2 to be used in a system 100 for detecting fiber damage in the dialyzer 2. The dialyzer 2 may have a body defining an interior 4 and an exterior 6. In addition, the dialyzer 2 may have dialysate ports 8,10 at the exterior of the dialyzer 6. Preferably, the dialyzer 2 has two dialysate ports, an inlet dialysate port 8 and an outlet dialysate port 10. The dialyzer 2 may also have fibers 12 within the interior 4 which house a fluid, such as, for example, blood, plasma, or the like. The fibers 12 may prevent fluids such as, for example, dialysate within the dialyzer 2 from contacting fluids within the fibers 12.

Figure 2:
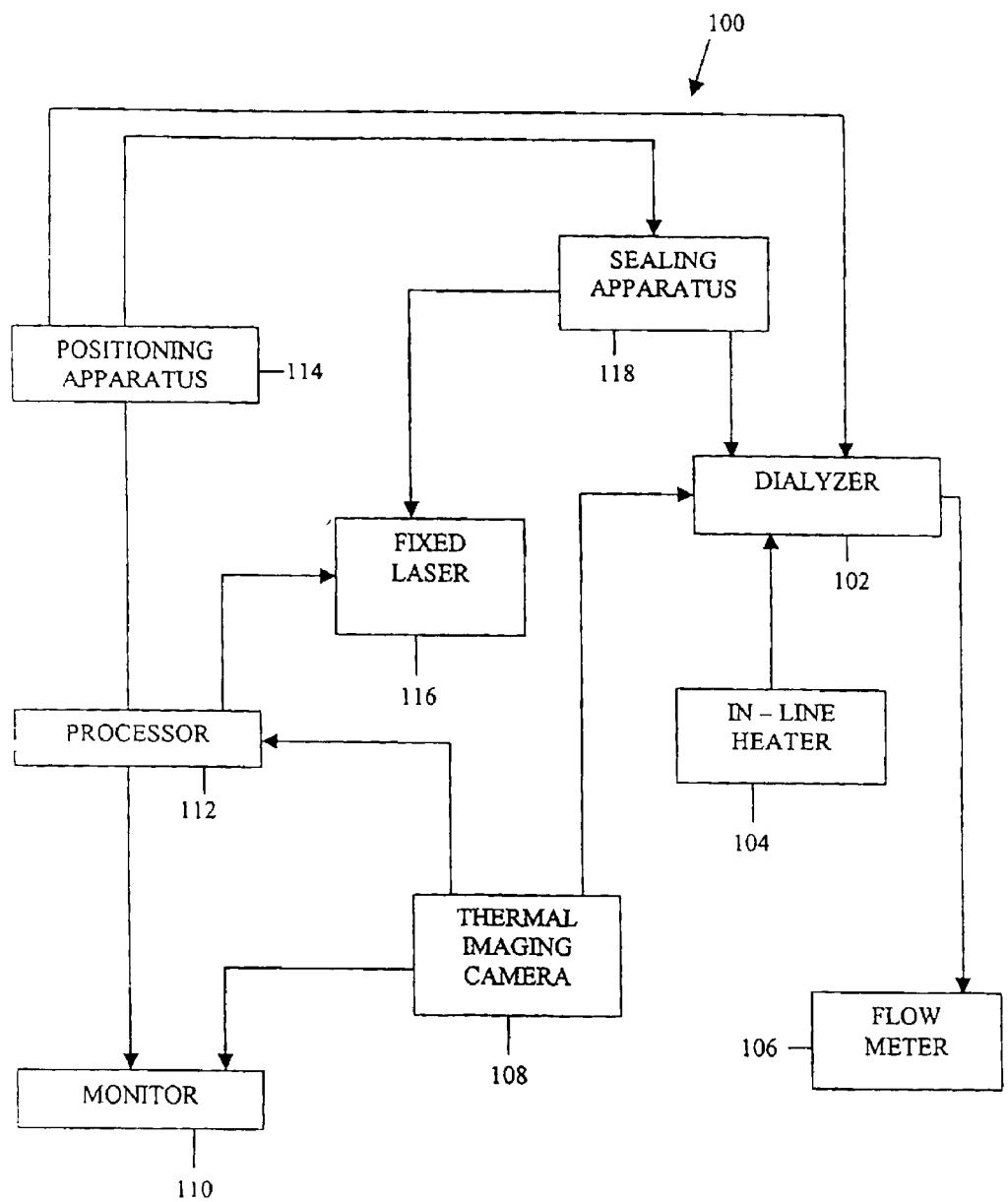
FIG. 2 illustrates a block diagram of a system for detecting fiber damage in a dialyzer in an embodiment of the present invention.

Referring now to FIG. 2, the system 100 may have an in-line heater 104 positioned adjacent to a first dialysate port 8 of the dialyzer 102. The in-line heater 104 may project a gas into the first dialysate port 8. The gas may exit from the second dialysate port 10. Preferably, the gas may be air; however, any non-combustible or non-toxic gas may also be implemented. The in-line heater 104 may maintain the projected air at a specific temperature. A flow meter 106 may be positioned adjacent to the second dialysate port 10 to control the air exiting the second dialysate port 10 and/or to create a pressure gradient within the dialyzer 102.

A thermal imaging camera 108 may be positioned adjacent to the dialyzer 102. The thermal imaging camera 108 may detect a variation in temperature at a surface 18 of the fiber 12. The temperature variations may signify that the air projected into the dialyzer 102 is leaking from the fiber 12. The thermal imaging camera 108 may be connected to a monitor 110 which may display any variations in temperature (described in further detail hereinafter) at the surface 18 of the fiber 12.

A processor 112 may be connected to the monitor 110 and the thermal imaging camera 108. The processor 112 may utilize a program for determining and/or recording an exact location of the temperature variation at the surface 18 of the fiber 12. The processor 112 may also be connected to a positioning apparatus 114. The positioning apparatus 114 may move the dialyzer 102 while in view of the thermal imaging camera 108 to determine the location of the fiber damage. The positioning apparatus 114 may be, for example, a robotic arm, which may be controlled by a user by, for example, a joystick. The positioning apparatus 114 may move the dialyzer 102 adjacent to a fixed laser 116 which may indicate the damaged area of the fiber 12 by projection of a laser stream. A sealing apparatus 118 may seal the damaged area of the fiber 12 at a point indicated by the fixed laser 116. In an embodiment, the sealing apparatus 118 may be a heated tip with which the user may contact the surface 18 of the damaged fiber 12.

Figure 3:
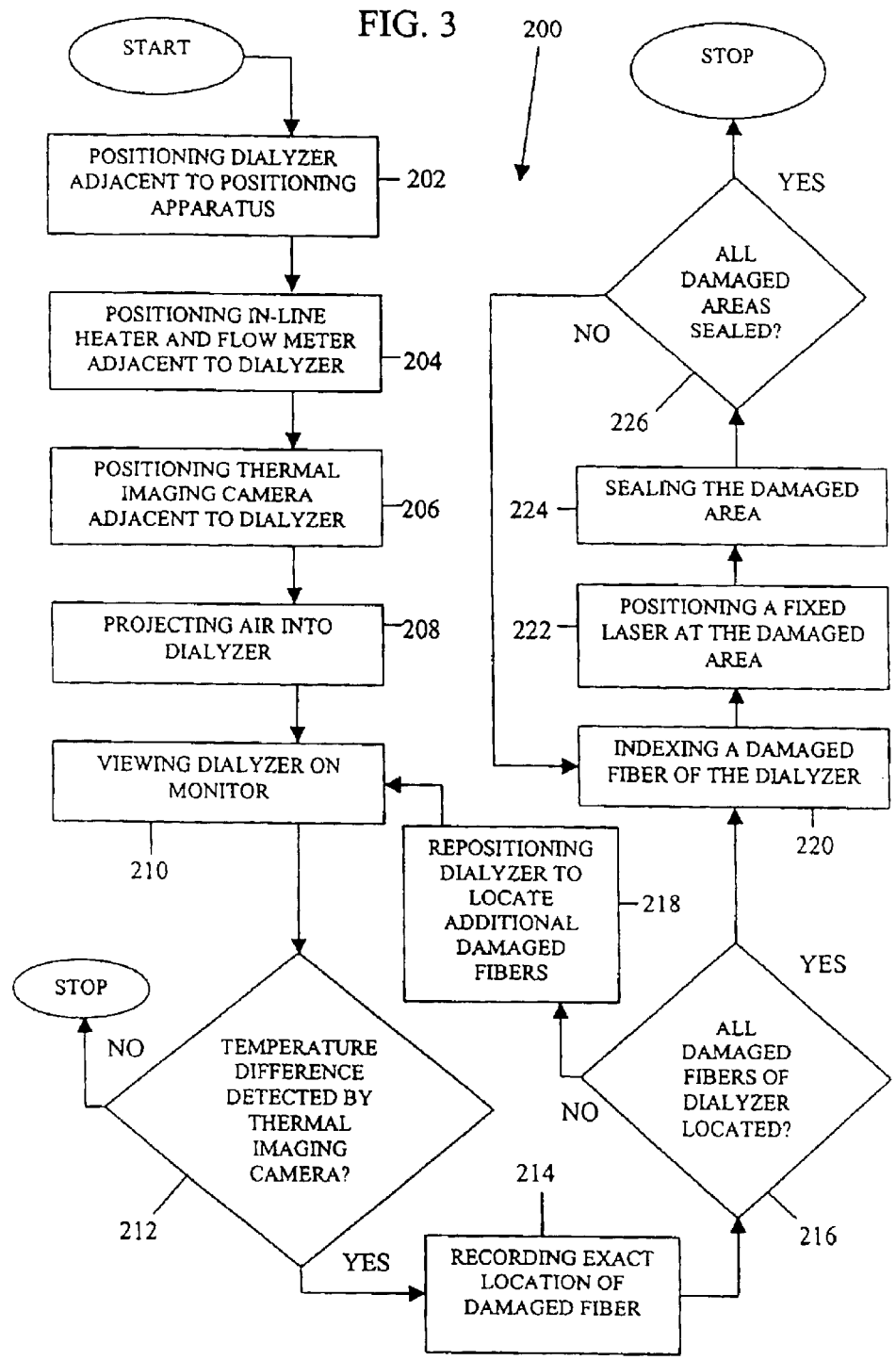
FIG. 3 illustrates a flowchart of a method for detecting fiber damage in a dialyzer in an embodiment of the present invention.

Referring now to FIG. 3, a flowchart is shown of a method 200 for detecting fiber damage in the dialyzer 102. The method 200 may have a first step 202 for positioning the dialyzer 102 adjacent to the positioning apparatus 114. The in-line heater 104 and the flow meter 106 may be positioned adjacent to the dialysate ports 8,10 of the dialyzer 102, as shown at step 204. The thermal imaging camera 108 may be positioned adjacent to the dialyzer 102, as shown at step 206.

The in-line heater 104 may project air into the dialyzer 102, as shown at step 208. The in-line heater 104 may maintain the air at a temperature different than a temperature of the dialyzer 102. To this end, in an embodiment, the dialyzer 102 may be heated prior to injection of air. The in-line heater 104 may maintain the air at a temperature lower than that of the dialyzer 102, such as, for example, room temperature. In another embodiment, the dialyzer 102 may be cooled prior to injection of air by, for example, placing the dialyzer 102 in a freezer or the like. The in-line heater 104 may maintain the air at a temperature higher than a temperature of the dialyzer 102, such as, for example, room temperature.

Figure 4:
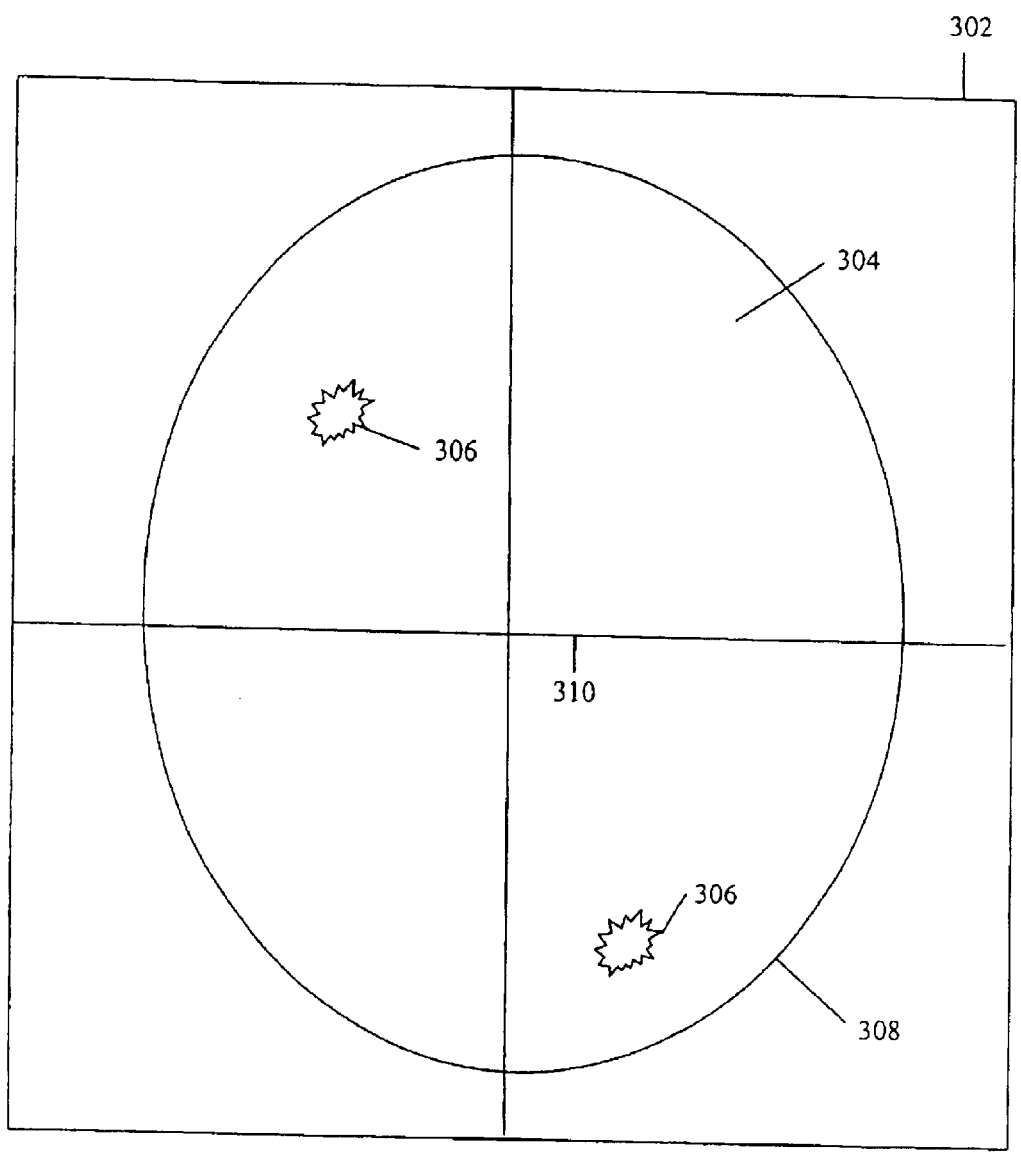
FIG. 4 illustrates a front plan view of a monitor in a system for detecting fiber damage in a dialyzer in an embodiment of the present invention.

An image 308 of the dialyzer 102 may then be viewed on the monitor 110, as shown at step 210 and illustrated in FIG. 4. A user may then determine whether a temperature difference is detected by the thermal imaging camera 108, as shown at step 212. The air entering the dialyzer 102 may be escaping through for example, a hole, in the damaged fiber 12. Accordingly, the thermal imaging camera 108 may detect a difference in temperature between a temperature at the surface 18 of the fiber 12 where the gas is escaping and a temperature of the dialyzer 2. The temperature difference may be represented on the monitor 302 by, for example, any one or more of areas 306. In an embodiment, the areas 306 may have a color that is different than a color used to represent a temperature at the surface 18 of the fiber 12. If a temperature difference is not present at the surface 18 of the fiber 12, the dialyzer 102 may not have leakage.

However, if the fiber 12 has a damaged area, a location of the temperature difference may be recorded by the processor 112, as shown at step 214. In an embodiment, the location of the damaged area may be recorded manually by the user. To this end, the user may move the dialyzer 102 using the positioning apparatus 114 while in view of the thermal imaging camera 108. The damaged area of the fiber 12 may then be displayed on the monitor 110. The dialyzer 102 may further be moved to align the displayed damaged area with an axis 310 present on the monitor 110. The user may then send a command to the processor 112 to record an X-Y coordinate of the damaged area. In another embodiment, the processor 112 may be programmed to record the location of a damaged area of the dialyzer 102.

The user may then determine if all damaged areas of the dialyzer 102 have been detected, as shown at step 216. The determination may be based on whether all areas of the dialyzer 102 have been examined. If all of the damaged areas have not been located, the positioning apparatus 114 may re-position the dialyzer 102, as shown at step 218. Re-positioning the dialyzer 102 may provide a different section of the dialyzer 102 for viewing by the thermal imaging camera 108. The user may then repeat the steps 210, 212 and 214 until all of the areas of the dialyzer 102 have been examined and all of the damaged areas have been located.

If no new coordinates can be recorded for the detected damaged areas of the dialyzer 102, all of the damaged areas of the dialyzer 102 may be considered located. The processor 112 may then index a first damaged area of the dialyzer 102, as shown at step 220. Accordingly, the processor 112 may cause the positioning apparatus 114 to move the dialyzer 102 into a path of the fixed laser 116, as shown at step 222. The fixed laser 116 may indicate to the user a first location where the fiber 12 is damaged. As a result, the user may seal the damaged area, as shown at step 224.

In an embodiment, the user may seal the dialyzer 102 by contacting the damaged area with a heated metal tip. Heat from the metal tip may cause an area surrounding the damaged area to melt the damaged area and seal any opening at which gas may be escaping. Other methods of sealing the dialyzer 102 are also contemplated, such as, for example, patching the damaged area, ultrasonic welding, or the like. The user may contact additional damaged areas of the dialyzer 102 with the heated metal tip. The user may then determine that all of the damaged areas requiring repair have been repaired, as shown at step 226. In an embodiment, the processor 112 may be programmed to independently operate the positioning apparatus 114 and the sealing apparatus 118. The damaged area may then be positioned for sealing and sealed without manual assistance.

In an embodiment, the user may position a paper filter (not shown) over the surface 18 of the fiber 12. Air escaping from the fiber 12 may cause a temperature change in the paper filter. The thermal imaging camera 108 may then detect a temperature difference between the temperature of the dialyzer 2 and a temperature of the paper filter.

Figure 5:
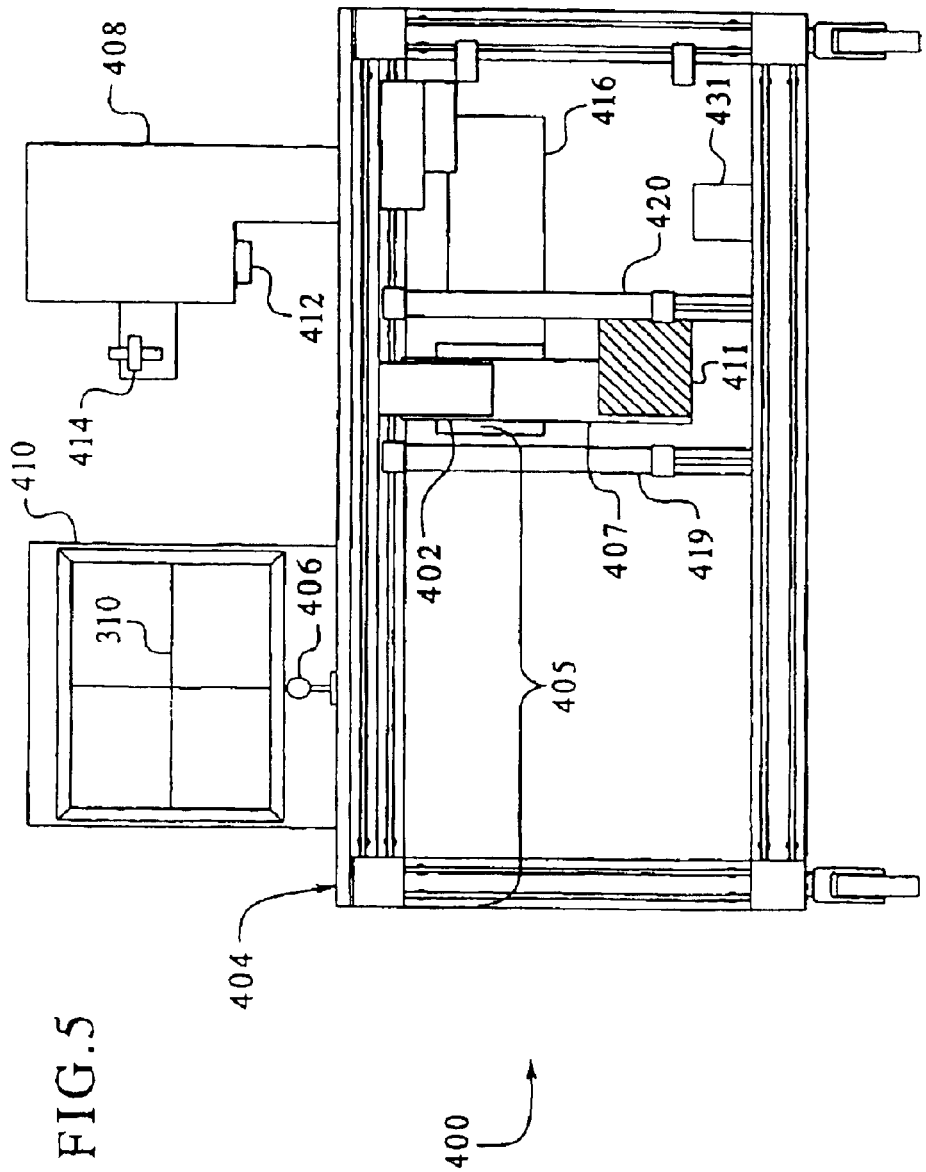
FIG. 5 illustrates a front plan view of a station having various components of a system for detecting fiber damage in a dialyzer in an embodiment of the present invention.

Referring now to FIG. 5, the system 100 of the present invention may be incorporated within a station 400 having a top surface 404. An area 405 may be provided at which a user may be present to operate the system 100. Adjacent to the area 405 and below the top surface 404 may be various components of the system 100. For example, the dialyzer 402 may be placed adjacent to the positioning apparatus 407. Movement of the dialyzer 402 may be controlled by a controller 406 positioned on the top surface 404 which may be connected to the positioning apparatus 407. The positioning apparatus 407 may also have a heat sink 411 which may remove heat transferred to the positioning apparatus 407 which may accumulate at the top surface 404 of the station 400. The in-line heater 416 may be positioned adjacent to the dialyzer 402 on a side of the dialyzer 402 opposite the user.

A light transmitter 419 and a sensor 420 may be provided on the station 400 wherein the dialyzer 402 is positioned between the light transmitter 419 and the sensor 420. The light transmitter 419 may transmit a light beam toward the sensor 420. If the light beam transmitted toward the sensor 420 is interrupted, movement of the positioning apparatus 407 may be paused as a safety precaution.

The thermal imaging camera 408 and the monitor 410 may be placed on the top surface 404 of the station 400. The thermal imaging camera 408 may have a lens 412 directed toward the top surface 404. An opening (not shown) may be provided within the top surface 404 below the lens 412. The dialyzer 402 may be moved by the positioning apparatus 407 wherein the dialyzer 402 is in alignment with the hole as well as the lens 412. The thermal imaging camera 408 may then obtain images of the dialyzer 402 for determining whether fiber damage exists in the dialyzer 402.

A fixed laser 414 may be adjacent to the thermal imaging camera 408. An opening (not shown) may be provided in the top surface 404 below the fixed laser 414. The user may move the dialyzer 402 using the positioning apparatus 407 wherein the dialyzer 402 is in alignment with the opening. Moreover, the user may align the dialyzer with the fixed laser 414 in accordance with a location of the damaged area indexed by the processor 112. As a result, the fixed laser 414 may extend to the dialyzer 402 and indicate the damaged area of the dialyzer 402. The user may then contact the indicated damaged area with a heated metal tip. As a result, the damaged area may be repaired.

In an embodiment, a heat source 431 may be provided adjacent to and below the heat sink 411. The heat source 431 may be, for example, a metal plate which may be heated prior to injection of gas into the dialyzer 402. The heat source 431 may enable the thermal imaging camera 408 to detect edges of the dialyzer 402. As a result, the monitor 410 may display the heat source 431 as an area surrounding the dialyzer 402 which may be brighter than a remainder of the display. The brighter area may assist the user in identifying areas 306 displayed by the monitor 410 which signify damaged areas of the dialyzer 402.

The system and the method of the present invention may require the use of a clean, processed gas, preferably air, within the dialyzer 102. As a result, the system and the method of the present invention may eliminate sterility concerns. In addition, the system and the method of the present invention may enable a user to locate a damaged area of the dialyzer 102 using the monitor 110 and the thermal imaging camera 108. A temperature difference at a surface of a damaged area of the dialyzer 102 may be represented on the monitor 110 as a distinct area, which enables the user to identify damaged areas.

Moreover, the fixed laser 116 indicates to a user the location of the damaged area. The user may then efficiently locate the damaged area when repairing the same. Use of the positioning apparatus 114 to change a position of the dialyzer 102 enables the dialyzer 102 to remain free of contaminants.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims.

We claim:

1. A method for detecting fiber damage in a dialyzer having a body defining an interior and further having a fiber having an interior wherein the fiber is within the interior of the dialyzer and wherein the fiber has a damaged area, the method comprising the steps of:

transmitting a gas into the interior of the fiber wherein the gas is at a temperature different from a temperature of the dialyzer and wherein the gas exits the fiber through the damaged area; and detecting a difference in temperature between a temperature of a surface of the fiber where the gas is exiting the damaged area and the temperature of the dialyzer.

2. The method of claim 1 further comprising the step of: displaying the difference in temperature on a monitor.

3. The method of claim 1 further comprising the step of: heating the dialyzer prior to transmitting the gas into the interior of the dialyzer.

4. The method of claim 1 further comprising the step of: cooling the dialyzer prior to transmitting the gas into the interior of the dialyzer.

5. The method of claim 1 further comprising the step of: directing a laser toward the location of the damaged area.

6. The method of claim 1 further comprising the step of: recording the location of the damaged area of the dialyzer.

7. The method of claim 1 further comprising the step of: controlling the gas transmitted into the interior of the fiber.

8. The method of claim 1 further comprising the step of: moving the dialyzer to locate the difference in temperature.

9. The method of claim 1 further comprising the step of: indexing the location of the damaged area.

10. The method of claim 1 further comprising the step of: repairing the damaged area.

11. The method of claim 1 further comprising the step of: sealing the fiber.

12. The method of claim 1 further comprising the step of: contacting the damaged area with a heated tip.

13. The method of claim 1 further comprising the step of: varying the temperature of the gas.

14. A system for detecting a damaged area, the system comprising:

a dialyzer having an interior and further having a fiber within the interior wherein the fiber is defined by an interior and wherein the fiber has a damaged area through which a gas may escape;

a heater which transmits the gas into the interior of the fiber; and a thermal imaging camera which detects a difference in temperature between a temperature at a surface of the fiber where the gas is exiting the damaged area and a temperature of the dialyzer.

15. The system of claim 14 further comprising:

a monitor connected to the thermal imaging camera.

16. The system of claim 14 further comprising:

a heat sink adjacent to the dialyzer.

17. The system of claim 14 further comprising:

a positioning apparatus for moving the dialyzer adjacent to the thermal imaging camera.

18. The system of claim 14 further comprising:

a laser adjacent to the thermal imaging camera wherein the laser indicates the location of the damaged area.

19. A method for determining a location of a damaged area of a dialyzer, the method comprising the steps of:

creating a temperature change in an interior of the dialyzer;

viewing a location of the temperature change; and assigning a coordinate to the location of the change in temperature.

20. The method of claim 19 further comprising the step of: indexing the coordinate.

* * * * *